US 9,446,147 B2

(12) United States Patent
Bong

(10) Patent No.: US 9,446,147 B2
(45) Date of Patent: Sep. 20, 2016

(54) MEMBRANE STABILIZING COMPOSITIONS AND METHODS

(75) Inventor: Dennis Bong, Columbus, OH (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 13/404,852

(22) Filed: Feb. 24, 2012

(65) Prior Publication Data
US 2012/0220668 A1 Aug. 30, 2012

Related U.S. Application Data

(60) Provisional application No. 61/446,383, filed on Feb. 24, 2011.

(51) Int. Cl.
*A61K 47/48* (2006.01)
*A61K 9/127* (2006.01)
*C07H 1/00* (2006.01)
*C07H 15/14* (2006.01)
*C07H 15/18* (2006.01)

(52) U.S. Cl.
CPC ....... *A61K 47/48815* (2013.01); *A61K 9/1271* (2013.01); *A61K 9/1272* (2013.01); *C07H 1/00* (2013.01); *C07H 15/14* (2013.01); *C07H 15/18* (2013.01)

(58) Field of Classification Search
CPC .. A61K 9/127; A61K 9/1271; A61K 9/1272; A61K 47/48815; C07H 15/18; C07H 1/00; C07H 15/14
See application file for complete search history.

(56) References Cited

U.S. PATENT DOCUMENTS

| 4,534,899 A | 8/1985 | Sears |
| 6,262,029 B1 * | 7/2001 | Press et al. ............. 514/26 |
| 6,319,517 B1 | 11/2001 | Cavallo et al. |
| 6,831,173 B1 * | 12/2004 | Jetten et al. ............. 536/123.1 |
| 7,749,520 B2 | 7/2010 | Davidsen et al. |

OTHER PUBLICATIONS

Harland, C. W., Botyanszki, Z., Rabuka, D., Bertozzi, C. R., & Parthasarathy, R. (2009). Synthetic trehalose glycolipids confer desiccation resistance to supported lipid monolayers. Langmuir, 25(9), 5193-5198.*

(Continued)

*Primary Examiner* — Eric Olson
*Assistant Examiner* — Dale R Miller
(74) *Attorney, Agent, or Firm* — Wood, Herron & Evans, LLP

(57) ABSTRACT

A sugar-anchor polymer and methods of making and using the same to stabilize a lipid membrane. The sugar-anchor polymer includes a sugar covalently bound to a first anchor and a second anchor wherein the covalent bonds are selected from the group consisting essentially of an oxime bond, a hydrazone bond, an acylhydrazide bond, an aminothioacetal bond, an acetal bond, a thioacetal bond, a dithioacetal bond, a thioether bond and combinations thereof. The method includes reacting a sugar having at least two nucleophilic moieties with at least two anchors, each anchor having at least one electrophilic moiety, to form the polymer. Alternatively, the method includes reacting a sugar having at least two electrophilic moieties with at least two anchors, each anchor having at least one nucleophilic moiety, to form the polymer. The anchors may be lipids or peptides. The sugar-anchor polymers stabilize lipid membranes against serum proteins, dehydration, and cryopreservation.

9 Claims, 14 Drawing Sheets

(56) References Cited

OTHER PUBLICATIONS

Immordino, M. L., Dosio, F., & Cattel, L. (2006). Stealth liposomes: review of the basic science, rationale, and clinical applications, existing and potential. International journal of nanomedicine, 1(3), 297.*

Carmona, S., Jorgensen, M. R., Kolli, S., Crowther, C., Salazar, F. H., Marion, P. L., . . . & Miller, A. D. (2009). Controlling HBV replication in vivo by intravenous administration of triggered PEGylated siRNA-nanoparticles. Molecular pharmaceutics, 6(3), 706-717.*

Ma, M., Chatterjee, S., Zhang, M., & Bong, D. (2011). Stabilization of vesicular and supported membranes by glycolipid oxime polymers. Chemical Communications, 47(10), 2853-2855.*

Niederhafner, P., Šbestík, J., & Ježk, J. (2008). Glycopeptide dendrimers. Part I. Journal of Peptide Science, 14(1), 2-43.*

Teramoto, Naozumi, et al., Trehalose and Trehalose-based Polymers for Environmentally Benign, Biocompatible and Bioactive Materials, Molecules, 2008, pp. 1773-1816, vol. 13, www.mdpi.org/molecules.

* cited by examiner

SEQUENCE LISTING

```
<160> NUMBER OF SEQ ID NOS: 3

<210> SEQ ID NO 1
<211> LENGTH: 23
<212> TYPE: PRT
<213> ORGANISM: Artificial Sequence
```

```
<220> FEATURE:
<223> OTHER INFORMATION: XENOPUS

<400> SEQUENCE: 1

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 2
<211> LENGTH: 24
<212> TYPE: PRT
<213> ORGANISM: Human immunodeficiency virus

<400> SEQUENCE: 2

Ala Val Ile Gly Ile Gly Ala Leu Phe Leu Gly Phe Leu Gly Ala Ala
1               5                   10                  15

Gly Ser Thr Met Gly Ala Arg Ser
            20

<210> SEQ ID NO 3
<211> LENGTH: 20
<212> TYPE: PRT
<213> ORGANISM: Influenza virus

<400> SEQUENCE: 3

Gly Leu Phe Gly Ala Ile Ala Gly Phe Ile Glu Asn Gly Trp Glu Gly
1               5                   10                  15

Met Ile Asp Gly
            20
```

MEMBRANE STABILIZING COMPOSITIONS AND METHODS

CROSS-REFERENCE TO RELATED APPLICATION

This application claims the filing benefit of U.S. Provisional Patent Application Ser. No. 61/446,383 filed Feb. 24, 2011, the disclosure of which is hereby expressly incorporated by reference herein in its entirety.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant Nos. NSF-0747194 and NSF-0927778 awarded by the National Science Foundation.

FIELD

The present invention relates generally to compositions and methods useful stabilizing membranes and more particularly to compositions and methods useful for stabilizing lipid membranes.

BACKGROUND

Lipid vesicles can function as carriers for bioactive agents. However, the utility of lipid vesicles as long circulating carriers has been limited by the general fragility of liposomes with regard to binding and lysis by serum proteins. Previous studies on polymerization-stabilization of lipid vesicles have utilized alkene or diacetylene polymerization in the headgroup or lipid anchor region. Due to the concomitant changes in lipid and headgroup packing, these methods yield lipid membranes with significantly non-native properties such as increased permeability and decreased fluidity.

More recently, membrane-anchored polyacrylates have been added to pre-formed vesicles and cross-linked in situ by EDC and a diamino linker, yielding a protected, polyanionic liposome. High negative surface charge limits carriers of this type for scavenging uptake mechanisms in vivo rather than circulation. Moreover, a synthetic limitation arises due to the requirement for post-crosslinking purification.

Surface neutral polymer-protected "stealth" vesicles function as long-circulating carriers and have been successfully implemented as drug carriers, featuring singly-anchored polyethylene glycol chains (PEG). The incorporation of lipid-anchored PEG into lipid vesicle membranes blocks serum proteins from binding to the vesicle, thus preventing lipid extraction, opsonization, and immunoclearance. However, PEG lipid vesicles do not tolerate dehydration and thus are not useful for long-term anhydrous storage of therapeutic agents included with the lipid vesicle.

Trehalose is a naturally occurring disaccharide of glucose with 1,1($\alpha$, $\alpha'$) linkage that protects biomembranes from desiccation and has been implicated as a key factor in the survival of microorganisms under anhydrobiotic conditions. Recent reports have documented the ability of both free trehalose and membrane-anchored trehalose, such as microbial trehalose mycolate (TDM) and its synthetic analog trehalose dibehenate (TDB), to protect and maintain the physical properties of synthetic supported lipid membranes. It has been further demonstrated that trehalose-functionalization can effectively block non-specific surface binding of serum proteins to trehalose-polymers. However, the previously used anchored trehalose compounds do not allow for the control or tuning of the stability of the lipid vesicle at the linkers used therein to meet specific operational requirements, such as acid sensitivity.

SUMMARY

While the invention will be described in connection with certain embodiments, it will be understood that the invention is not limited to these embodiments. On the contrary, the invention includes all alternatives, modifications and equivalents as may be included within the spirit and scope of the present invention.

Embodiments comprise a versatile, stabilized, lipid-vesicle based carrier for delivery of hydrophobic or hydrophilic cargo. Exemplary embodiments may be resistant to degradation and non-specific binding with serum proteins. Various embodiments may be used for selective systemic or depot delivery with long circulation and stability times. In some embodiments, carrier size may be modified. Exemplary embodiments are structurally stable under physiological conditions which allow for slow steady release of the cargo and sustained presence. The amphiphilic nature of various compositions permits their use to deliver hydrophobic cargo, such as small molecule drugs, as well as hydrophilic cargo, such as biologics.

An exemplary formulation permits targeting and extended release that may mitigate toxicity associated with various small molecule drugs. Thus, an embodiment loaded with a cargo, such as a therapeutic agent, that exhibits a poor distribution and toxicity profile may yield an enhanced therapeutic index resulting from the diminished toxicity. Exemplary carriers may be useful for targeted delivery of a wide range of therapeutic agents, for example, to tumor tissue for the treatment of cancer as well as treatment of inflammation such as results from autoimmune disease.

Embodiments may be useful as a general formulation for a wide range of therapeutics. In various embodiments, a sugar-anchor polymer such as a sugar-lipid polymer or a sugar peptide polymer, is used to produce a surface-stabilized lipid vesicle or liposome carrier that may carry cargo within the lipid membrane, within the aqueous compartment, or within both the membrane and the aqueous compartment. In some embodiments, a sugar derivative is used to crosslink lipid anchors to produce a highly branched sugar-lipid polymer with multiple lipid anchors rather than a single lipid anchor as used in PEG based stealth liposomes. Increased membrane anchoring may result in greater stability and extended circulation times. Increased circulation time may result in overall greater drug efficacy and reduce the dosage frequency. Embodiments may be applicable to any therapeutic for which slow systemic release is necessary and or helpful. Sustained release of this type may facilitate delivery of small molecule hydrophobic therapeutics across the blood-brain barrier.

In various embodiments, polymerization may be performed under native (mild aqueous buffer) conditions in situ post-encapsulation of a therapeutic or alternatively the sugar-lipid polymer may be prepared separately and added as a formulation component. The percentage incorporation of sugar-lipid polymer may tune surface stability, allowing the release times to be modulated as a function of sugar-lipid polymer content. Unlike previously known stabilized liposomes, the sugar-anchor polymer may use an acid-sensitive linkage that will slowly hydrolyze into the anchor (i.e., lipid or peptide) and sugar components that can be cleared from the system allowing for the release of cargo from the carrier. The use of these linkers allows for further tuning and control of stabilized liposomes. For example, this sensitivity may be used to exploit the acidic environment of tumor tissue to trigger release.

Thus, embodiments of the invention are directed to a sugar-anchor polymer, such as a sugar-lipid polymer or a sugar-peptide polymer, and methods of making and using the same to stabilize a lipid membrane. The sugar-anchor polymer includes a sugar covalently bound to a first anchor and a second anchor wherein the covalent bonds are selected from the group consisting essentially of an oxime bond, a hydrazone bond, an acylhydrazide bond, an aminothioacetal bond, an acetal bond, a thioacetal bond, a dithioacetal bond, a thioether bond and combinations thereof. In one aspect, the method of making the sugar-anchor polymer includes reacting a sugar having at least two nucleophilic moieties with at least two anchors, each anchor having at least one electrophilic moiety, to form the sugar-anchor polymer. Alternatively, the method of making the sugar-anchor polymer includes reacting a sugar having at least two electrophilic moieties with at least two anchors, each anchor having at least one nucleophilic moiety, to form the sugar-anchor polymer. The sugar-anchor polymers stabilize lipid membranes against serum proteins, dehydration, and cryopreservation.

BRIEF DESCRIPTION OF THE DRAWINGS

The accompanying figures, which are incorporated in and constitute a part of this specification, illustrate exemplary embodiments of the invention and, together with a general description of the invention given above, and the detailed description given below, serve to explain the principles of the invention.

DETAILED DESCRIPTION

Embodiments of the invention are directed to novel, improved, anchored sugar polymeric compositions, in particular sugar-lipid polymers and sugar-peptide polymers and to the methods of preparation and use of such compositions.

Figure 1:
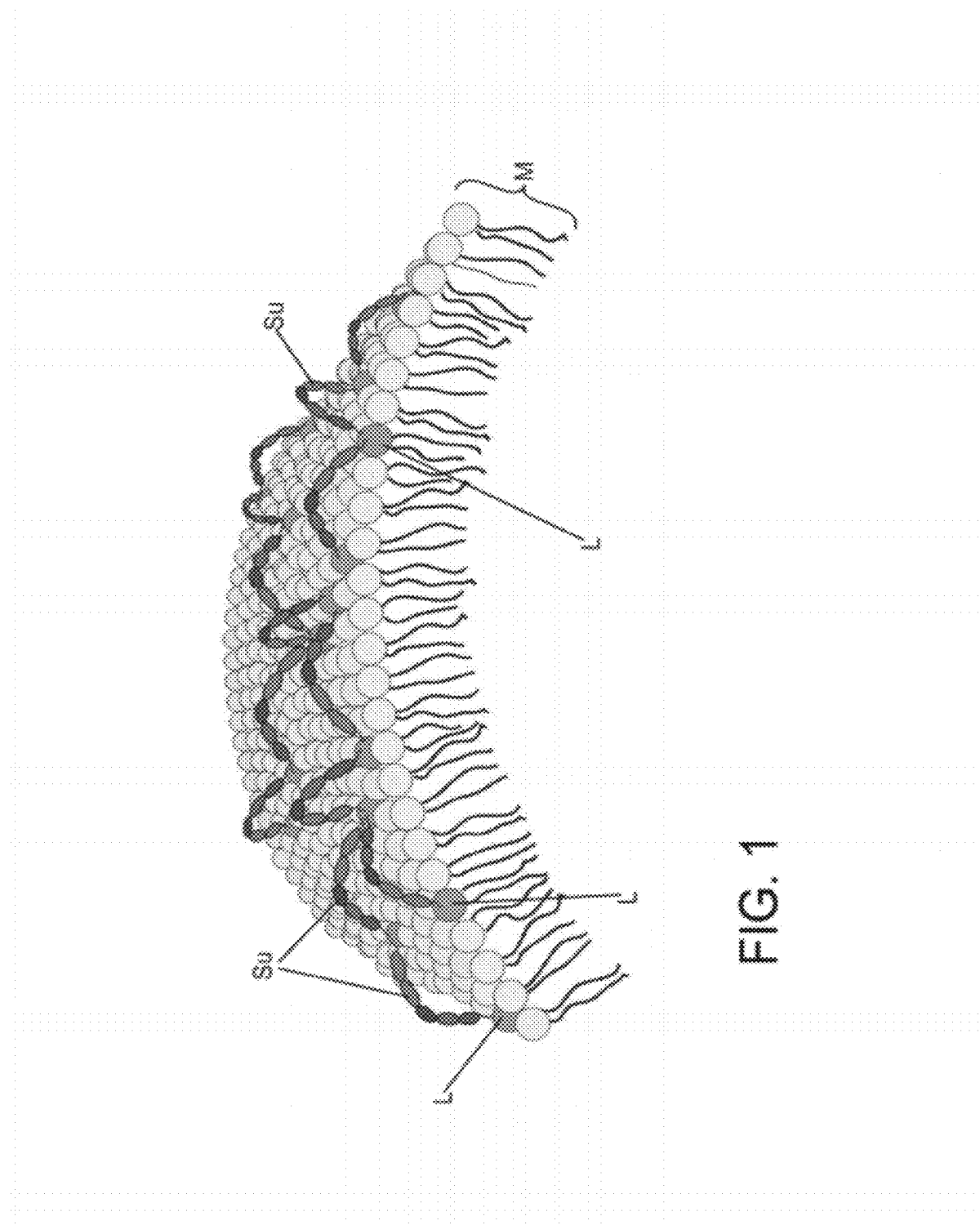
FIG. 1 illustrates the stabilization of a lipid membrane in accordance with embodiments of the invention.

With reference to FIG. 1, embodiments of the invention include methods and compositions for stabilizing a lipid membrane by cross-linking with a sugar Su at least two lipids L that may function as anchors in the lipid membrane M. The sugar Su includes at least two linker moieties that are capable of coupling to complimentary linker moieties on at least two lipids L in a non-enzymatic reaction.

In one embodiment, the linker moieties on the lipids L are nucleophilic moieties Nu and the linker moieties on the sugar Su are electrophilic moieties E, as illustrated by Formula 1 below:

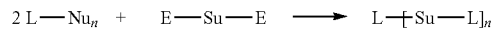

$$2\,L\text{—}Nu_n \;+\; E\text{—}Su\text{—}E \;\longrightarrow\; L\text{—}[Su\text{—}L]_n$$

wherein n represents a number of 1, 2, or 3. The nucleophilic moieties Nu are represented by Formulas 2 and 3 below:

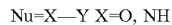

Nu=X—Y  X=O, NH

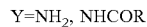

Y=NH$_2$, NHCOR or

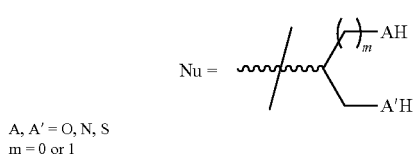

A, A' = O, N, S
m = 0 or 1 wherein X is bound to the lipid L and R represents hydrogen or an alkyl. A and A' each represent one of oxygen, nitrogen, or sulfur and can be the same or different. Exemplary nucleophilic moieties Nu that are complementary to the electrophilic moieties E of the sugar Su include aminooxyether to form oxime bonds between the lipid L and the sugar Su, hydrazines to form hydrazone bonds, acylhydrazines to form acylhydrazide bonds, aminothiols to form aminothioacetal bonds, diols to form acetal bonds, thioalkanols to form thioacetal bonds, dithiols to form dithioacetal bonds, and combinations thereof. These bonds have different sensitivity to being hydrolyzed in an acidic environment, which may be useful for targeting lipid vesicles to release their cargo in acidic environments such as found in tumor tissue or inflamed tissue.

Figure 2:
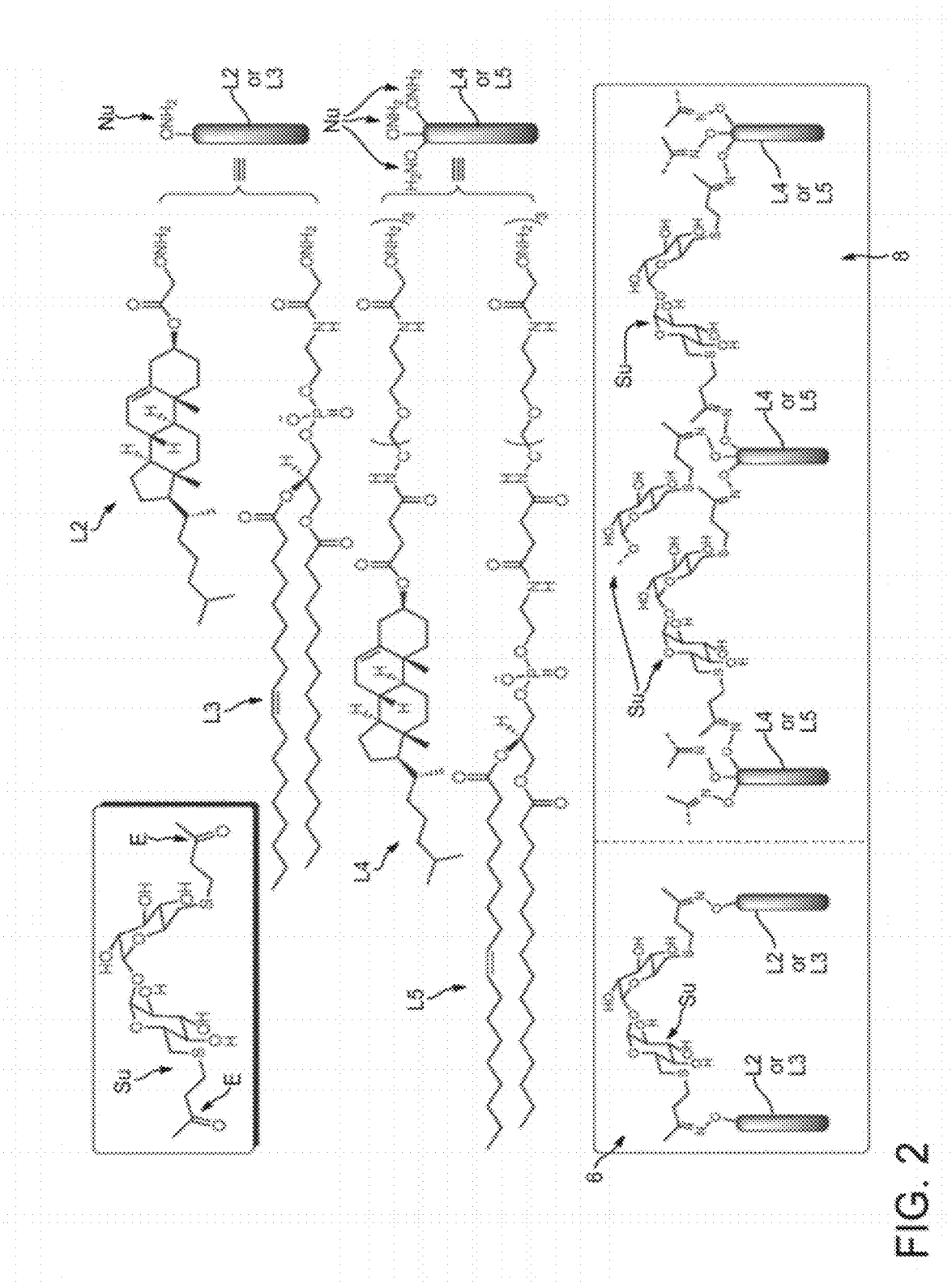
FIG. 2 illustrates the structure of exemplary functionalized lipids, and sugars, and the resulting sugar-lipid polymers in accordance with embodiments of the inventors.

The lipid L may include from 1 to 3 nucleophilic moieties Nu. In one embodiment, the lipid includes 1 nucleophilic moiety (Nu), such as the exemplary monoaminooxyether phospholipids identified as lipids L2 and L3 of FIGS. 2 and 3. The resulting sugar-lipid polymers (6 of FIG. 2) from such lipids L2, L3 will be dimers having two lipid L components linked by the sugar component Su. In an alternative embodiment, the lipid includes 2 or 3 nucleophilic moieties Nu, such as the exemplary trisaminooxyether lipids identified as lipids L4 and L5 of FIGS. 2 and 3. The resulting sugar-lipid polymers 8 and 9 from such lipids L4, L5 will have multiple lipids polymerized to one another. As used herein, the term "polymer" is understood to include sugar-lipid polymers that have two or more lipid (L) components.

Figure 3:
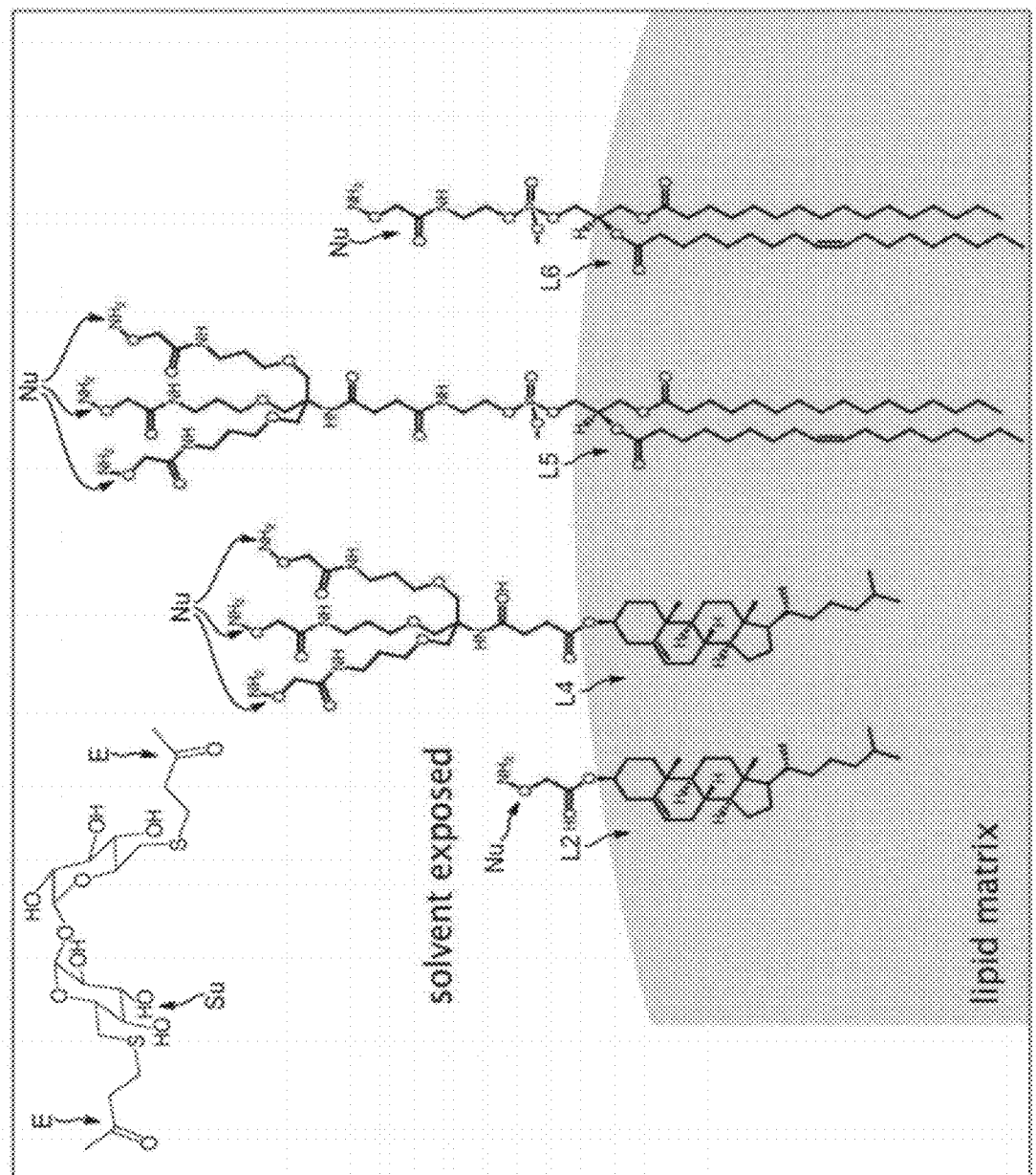
FIG. 3 illustrates the structure of exemplary functionalized lipids, and sugars, and the resulting sugar-lipid polymers in accordance with embodiments of the inventors.
Figure 4:
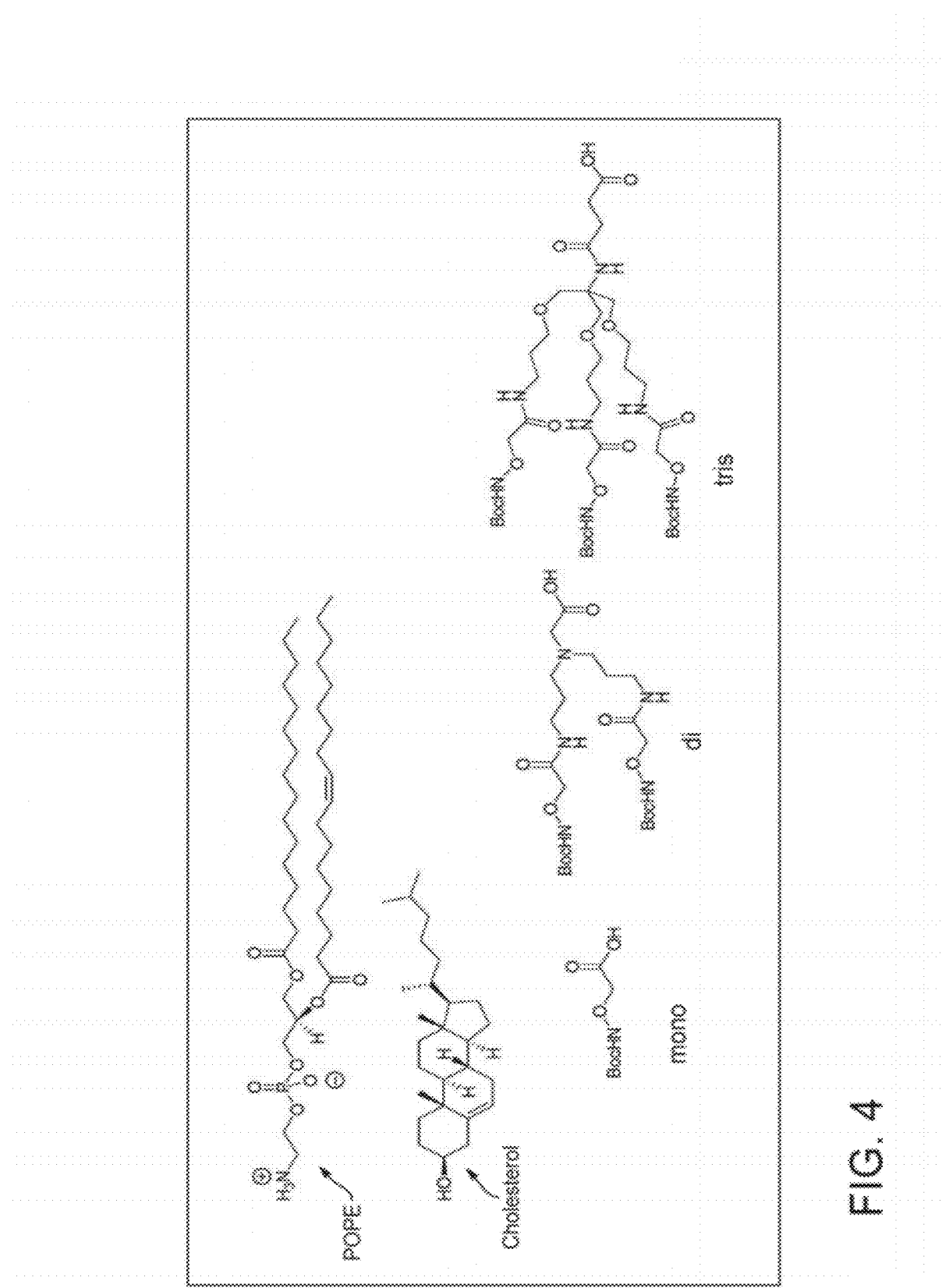
FIG. 4 illustrates the structures of exemplary native lipids and exemplary linking head groups in accordance with embodiments of the inventors.

Exemplary mono, di, and trisaminooxyether lipids may be prepared by acylation of a lipid, such as cholesterol or 1-palmitoyl-2-oleoyl-sn-glycero-3-phospho-ethanolamine (POPE), with Boc-protected aminooxyether headgroups (FIG. 4). Boc-cleavage with trifluoroacetic acid (TFA) yields aminooxyether lipid TFA salts, which may be directly reacted with electrophilic moieties E of the sugar in either water/methanol/chloroform mixtures or acidic aqueous buffer to cleanly produce oxime dimers from the monoaminooxyether lipids, and branched sugar-lipid oxime polymers from the di-aminooxyether lipids or tris-aminooxyether lipids. For example, the aminooxyether lipid TFA salts may react with the keto moiety of diketo-trehalose (Su of FIGS. 2 and 3) in either water/methanol/chloroform mixtures or acidic aqueous buffer to produce oxime dimer 6 and branched sugar-lipid oxime polymers 8. Lipids in addition to cholesterol and POPE may be used as lipid anchors in the present system. Different lipid anchors will impart new properties biophysically, but also biologically active anchors may be used. Thus, hydrophobic small molecules and membrane anchoring biologics may be used purely as membrane anchors or incorporated as a minority component. Lipid anchors may be varied to include, in addition to others, sterol anchors, sphingosine derivatives, saturated phospholipids, saturated diester lipids and diether lipids.

Figure 5:
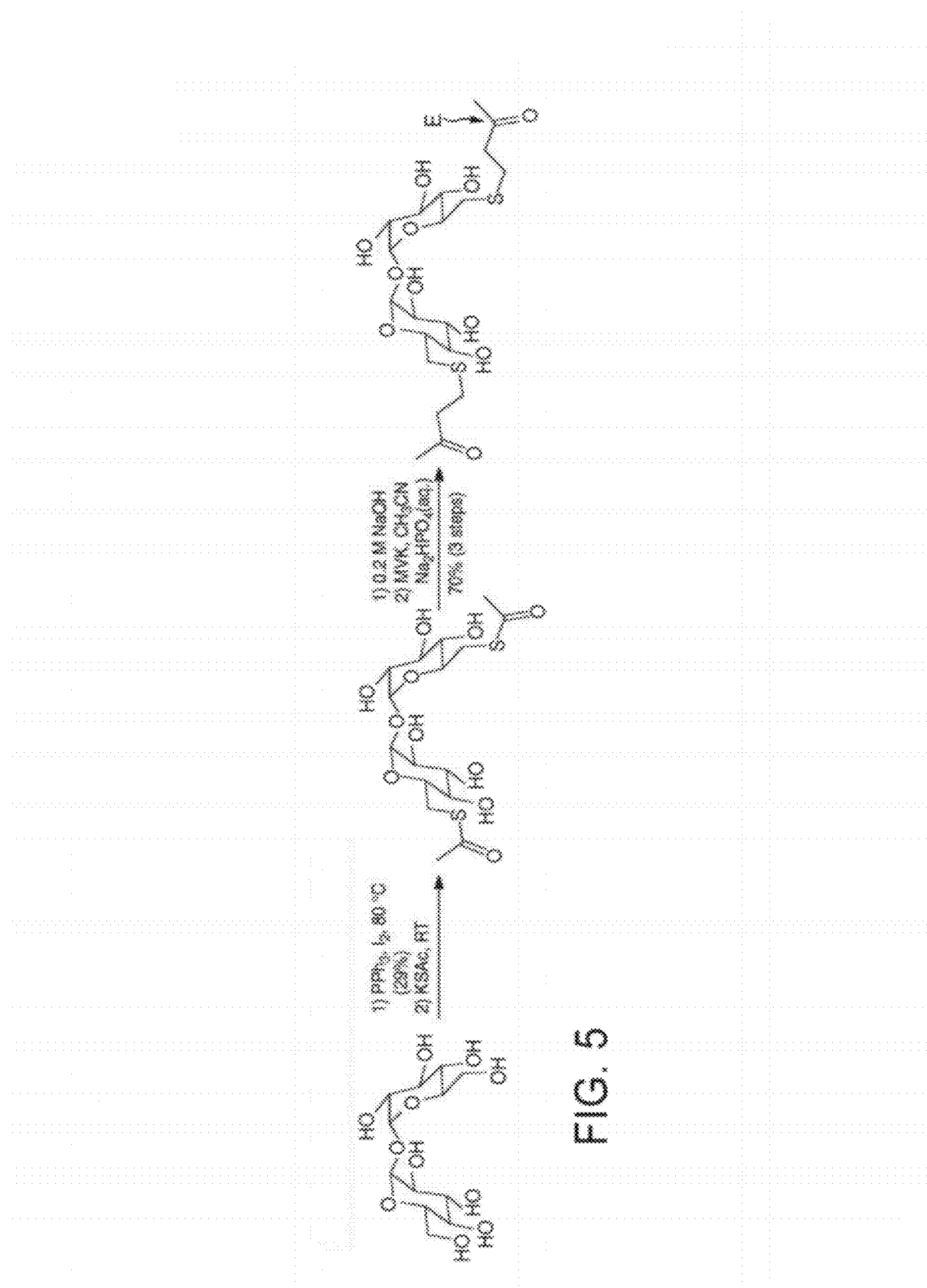
FIG. 5 illustrates the synthesis of an exemplary trehalose cross-linker in accordance with the embodiments of the inventors.

With reference back to Formula 1, the sugar Su has at least two electrophilic groups E. Native sugars may be functionalized to include the at least two electrophilic moieties E. In one embodiment, the sugar Su is a disaccharide, such as trehalose, which can be lipid anchored at the $C_6$ positions of the glucose monomeric subunits while maintaining its anti-desiccant function. In an exemplary embodiment illustrated in FIG. 5, diketo functionality may be attached to the $C_6$ positions by iodination of the $C_6$ primary alcohols followed by a high-yielding 3-step sequence of iodide displacement by potassium thioacetate, thiolester hydrolysis, and thiolate conjugate addition to methylvinyl ketone. The resulting diketo trehalose may then be reacted with first and second functionalized lipids (i.e., lipids having a nucleophilic moiety) to generate a sugar-lipid polymer as described above. Exemplary electrophiles (E) are represented by the formula below:

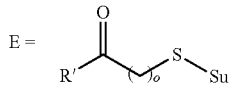

R' = H, alkyl
o = 1, 2, or 3

While the preferred sugar is the non-reducing disaccharide trehalose, other sugar moieties, may be employed, such as other disaccharides, monosaccharides and some oligosaccharides, to the extent that the other sugar moieties can be selectively functionalized to include the electrophilic moieties (or nucleophilic moieties) needed to form the sugar-anchor polymers.

The nucleophilic moieties Nu of lipids L may be reacted with the electrophilic moieties E on the sugar Su to form the sugar-lipid polymers. In one embodiment, the nucleophilic moieties Nu of lipids L is reacted with the electrophilic moieties E on the sugar Su under mildly acidic aqueous conditions, such as a pH range between about 5 pH to about 6 pH. Alternatively, the nucleophilic moieties Nu of lipids L are reacted with the electrophilic moieties E on the sugar Su in the presence of water/chloroform mixtures of about a 1:1 ratio.

In a complementary alternative embodiment, the linker moieties on the sugar Su are nucleophiles Nu' and the linker moieties on the lipids L are electrophiles E'. For example, the sugar Su may include two nucleophilic moieties Nu' and the lipid L may include from 1 to 3 electrophilic moieties E', as illustrated by Formula 4 below:

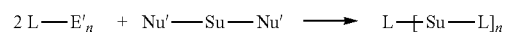

wherein n represents a number of 1, 2, or 3. The electrophilic moiety E' is represented by Formula 5 below:

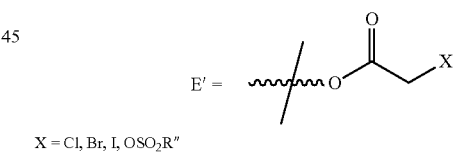

X = Cl, Br, I, OSO$_2$R'' wherein E' is attached to the lipid L by the ester linkage and R'' is an aryl group or an alkyl group.

With reference back to Formula 4, the nucleophilic moieties Nu' on the sugar Su may be a thiol, an amine, hydrazine, or amino-oxyether.

Figure 6:
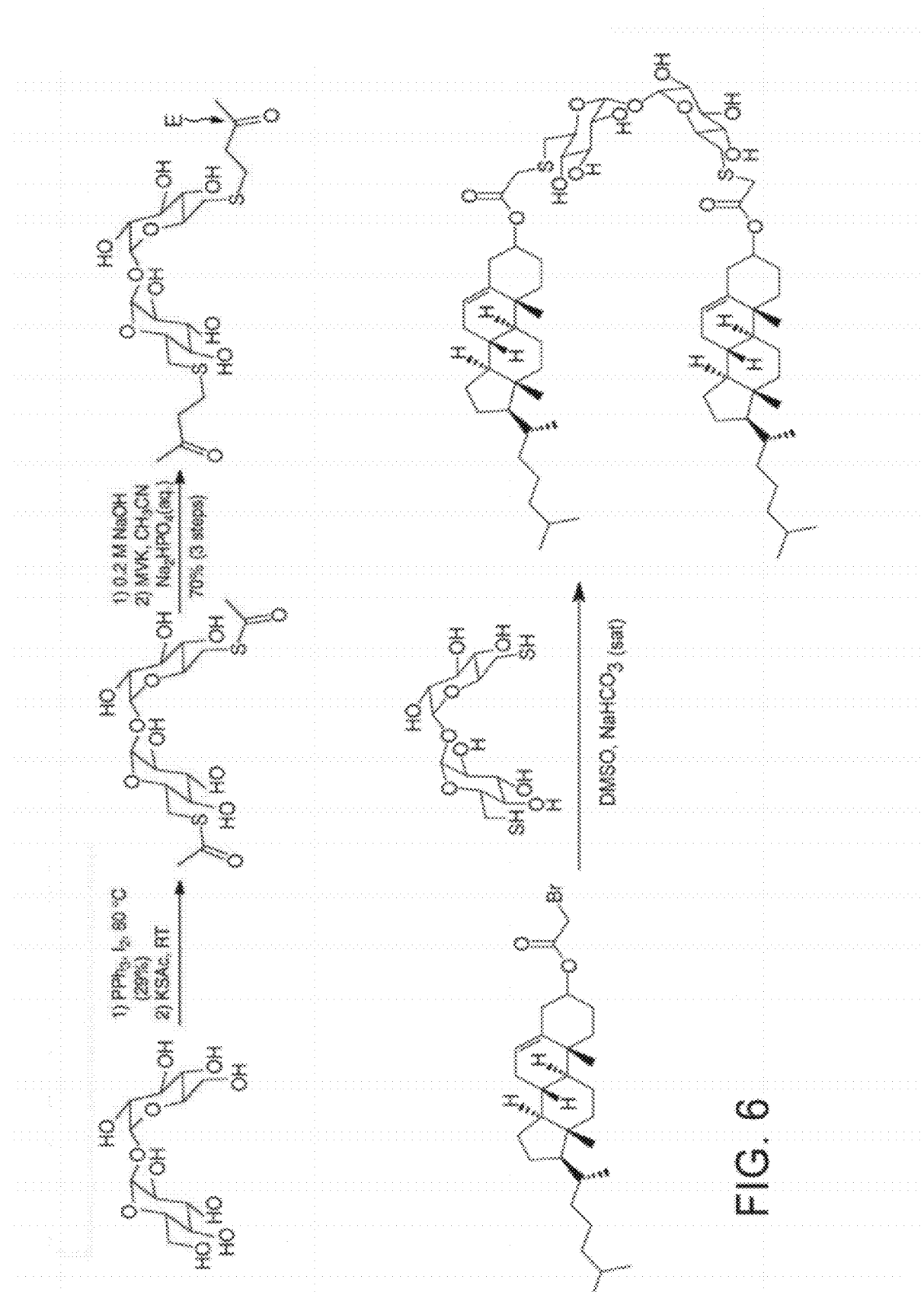
FIG. 6 illustrates the synthesis of a cholesterol thio ether dimer in accordance with the embodiments of the inventors.

In an exemplary embodiment illustrated by the formula illustrated in FIG. 6, the lipid, cholesterol, includes one ester electrophilic moiety E'. The exemplary sugar Su, trehalose, includes a thiol at the $C_6$ positions of each glucose monomeric subunit. The electrophilic moieties of the two lipids L may be reacted with the two nucleophilic moieties Nu' of the sugar Su in DMSO saturated with NaHCO$_3$ to form a trehalose-cholesterol thioether dimer.

Lipids in addition to cholesterol may be used as lipid anchors in the present embodiment, such as POPE. Different lipid anchors will impart new properties biophysically, but also biologically active anchors may be used. Thus, hydrophobic small molecules and membrane anchoring biologics may be used purely as membrane anchors or incorporated as a minority component. Lipid anchors may be varied to include, in addition to others, sterol anchors, sphingosine derivatives, saturated phospholipids, saturated diester lipids and diether lipids.

In an alternative embodiment of the sugar-anchor polymer, the lipid anchor L may be replaced with a peptide anchor. Exemplary peptides that may be used as anchors include peptides derived from transmembrane domain proteins, antimicrobial peptides, channel forming peptides, fusogenic peptides, and signaling peptides. Examples of native peptide anchors include the magainin peptides (SEQ ID NO 1: GIGKFLHSAKKFGKAFVGEIMNS), the HIV fusion peptide sequence (SEQ ID NO 2: AVIGIGALFLG-FLGAAGSTMGARS), the Influenza viral fusion peptide sequence (SEQ ID NO 3: GLFGAIAGFIENGWEGMIDG), as well as the many synthetic derivations of these sequences and synthetic cationic membrane active peptides and peptoids. As an example of this embodiment, the synthetic peptide anchor may be N-terminally acylated with an electrophilic moiety such as a maleimide or broacetyl group, which allows coupling to the a nucleophilic moiety on the sugar, such as the trehalose dithiol as previously described. Nucleophilic addition by the sugar thiol derivative would generate a stable thioether bond. The sugar-peptide polymers confer stability to lipid membranes in a manner similar to the stability conferred by the sugar-lipid polymers. Thus, the sugar-peptide anchors may be used in a similar manner to confer similar protective benefits to a lipid membrane.

The methods described herein result in sugar-anchor polymers, such as sugar-lipid polymers and sugar-peptide polymers, that may be incorporated into lipid membranes to stabilize such membranes against serum proteins and antibodies, as well as against the rigors of dehydration and cryopreservation. The sugar-lipid polymers may be incorporated into a lipid membrane with either a pre-formed sugar-lipid polymers or by polymerizing lipids in situ with the sugar after the membrane is formed. For example, the pre-formed sugar-lipid polymer may be dissolved in an organic solvent, such as chloroform or chloroform-methanol mixtures, and dried along with organic solvent solutions of lipids into a film. Rehydration of the film with an aqueous buffer would then yield the polymer-incorporated liposome. Alternatively, an organic solution of pre-formed sugar-lipid polymer and other lipids for the membrane can be vortexed with aqueous buffer and then the organic solvent may be evaporated, in a reverse-emulsion liposome preparation method. Other methods of forming lipid membranes may be employed using the sugar-lipid polymers as will be appreciated by the skilled artisan. With regard to in situ polymerization, the polymer may be selectively formed on the outside of a lipid membrane, such as the membrane of a liposome, using in situ polymerization of pre-formed and sized liposomes. For example a functionalized sugar such as a diketo trehalose, may be added to the liposomes containing the functionalized lipids, such as aminooxy lipids, under conditions that promote polymerization, such as at a pH range of about 5 to about 6 and incubated for about 12 to about 14 hours. Similar methods may be employed with the sugar-peptide polymers.

In exemplary embodiments, the lipid membranes may be loaded with up to 30 mole percent sugar-anchor polymers. In alternative embodiment, the lipid membranes are loaded with the sugar-anchor polymer in a range between about 10 mole percent to about 30 mole percent. Higher concentrations of sugar-anchor polymer loading into the lipid membrane generally confer greater protection to the lipid membrane.

Hydrophilic and hydrophobic cargo may be loaded into lipid vesicles using routine techniques as known by those of ordinary skill in the art. For example, hydrophilic cargo may be included in the hydrating buffer of either the film hydration or reverse emulsion method. In another example, hydrophobic cargo may be loaded into a lipid vesicle that includes embodiments of the lipid-sugar polymer using the film hydration method with the cargo as one component of the mixed lipid/lipid-sugar polymer film. In a further example, charged cargo may be driven into the liposomal compartment using remote loading strategies that exploit ion gradients and osmotic pressure to yield high intraliposomal concentrations of cargo.

Stabilized membrane assemblies may be loaded with therapeutic, imaging and targeting cargo and thus have a number of potential uses including but not limited to: diagnostics, delivery of imaging and contrast agents, immunogens, adjuvants, vaccines, passive carriers, targeted carriers and controlled release carriers. The stabilized lipsomes were resistant to degradation during dehydration and cryo preservation and the stability may be turned by controlling the percent incorporation of the sugar-lipid polymer in the membrane as well as by the selection of the linker bonds between the sugar and lipid components.

Additionally, stabilized membranes may be used to develop robust lipid membrane based biosensors which currently are limited due to the fragility of the lipid membrane. There are numerous analytical and nanochemistry applications based on membrane proteins, including but not limited to ion channel based sensors, signal transduction protein-based sensors, cell-adhesion based sensors that could be enhanced with membranes that include embodiments of the sugar-anchor polymer, such as the sugar-lipid polymer or the sugar-peptide polymer described herein.

The present disclosure is further illustrated by the following Examples, which should not be construed as further limiting. The contents of all figures and all references, patents, and published patent applications cited throughout this disclosure are expressly incorporated herein by reference to their entirety.

Example 1

Native trehalose-lipids were lipid-anchored at the C6 positions of the glucose. These convenient sites on trehalose were chosen for regioselective attachment of diketo functionality by iodination of the C6 primary alcohols followed by a high-yielding 3-step sequence of iodide displacement by potassium thioacetate, thiolester hydrolysis and thiolate conjugate addition to methylvinyl ketone. The diketo trehalose was then reacted with an aminohydroxy lipid to generate oxime-linked trehalose lipid derivatives. Two lipid anchors were explored, unsaturated phospholipid POPE and cholesterol. These anchors were readily acylated using mono, di, and tri-functionalized amino-hydroxy headgroups designed to produce a discrete lipid oxime-dimer, linear oxime-lipid polymer and branched oxime-lipid polymer, respectively.

Mono and trisaminooxyether lipids were prepared by acylation of cholesterol or POPE with Boc-protected aminooxyether headgroups (FIGS. 3 and 4). Boc-cleavage with trifluoroacetic acid yielded the aminooxyether lipid TFA salts, which were directly reacted with diketo-trehalose 1 in either water/methanol/chloroform mixtures or acidic aqueous buffer to cleanly produce oxime dimers from the mono-amino-oxyether lipids, and branched sugar-lipid oxime polymers from the tris-aminooxyether lipids.

All aminohydroxy phospholipid and cholesterol anchors successfully formed oxime linkages with the diketo-trehalose, forming both oxime dimers and polymers. These oxime products were soluble in organic solvents, allowing the preparation of polymer/lipid vesicles from hydration of mixed lipid films.

Another the cholesterol lipid anchor was used to form a slightly different trehalose lipid dimer (FIG. 6). The dimer was a cholesterol ester similar to the previous cholesterol oxime dimer, though the oxime linkage and the three associated carbons have been removed, giving a cholesterol thioglycolate ether dimer with trehalose.

Figure 7:
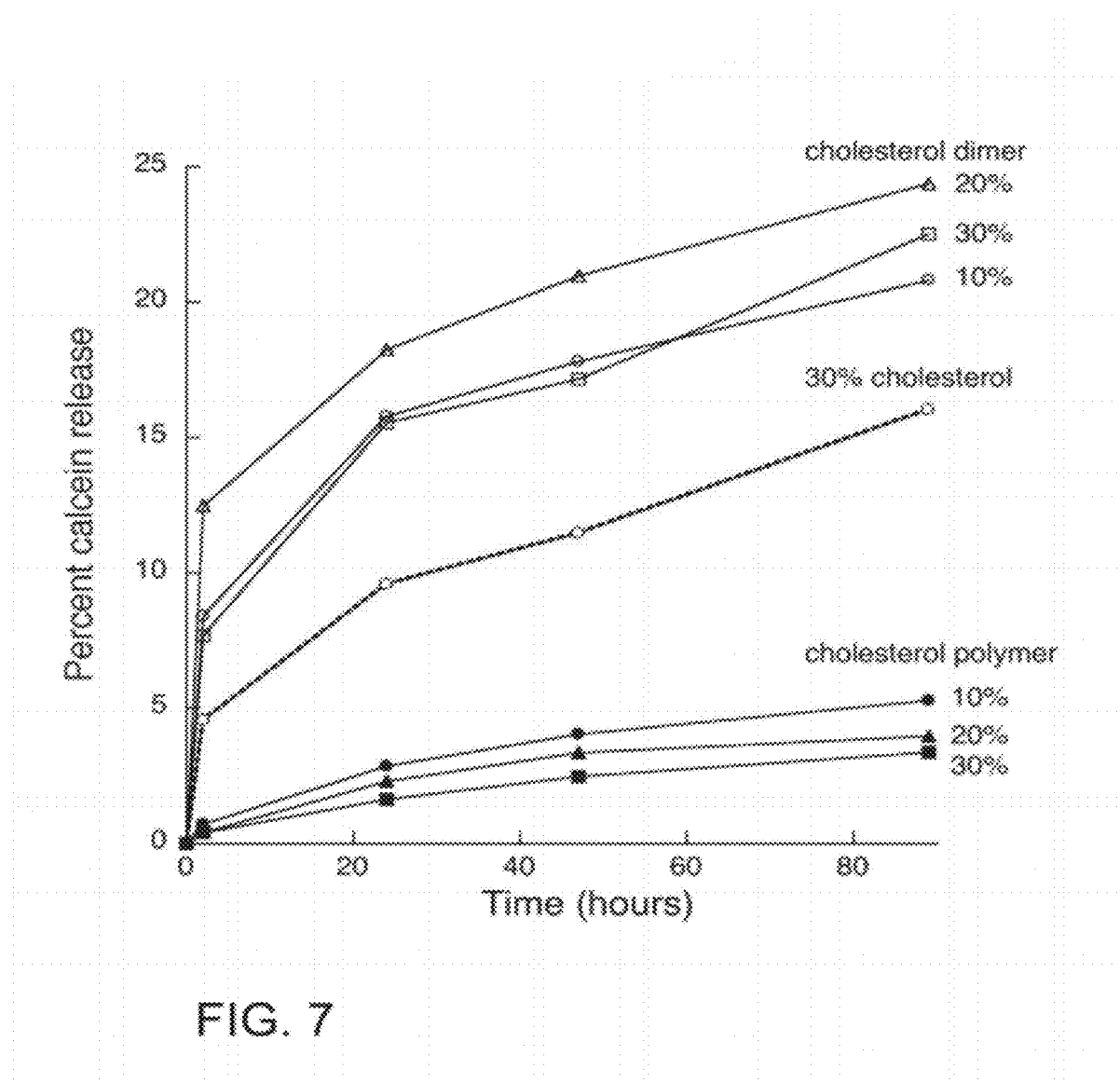
FIG. 7 is a graph illustrating improved liposome stability in accordance with the embodiments of the inventors.

Vesicles loaded with calcein at self-quenched concentration were prepared by hydration of egg PC/polymer films with calcein-containing buffer followed by gel filtration. Notably, the cholesterol-derived polymers were much more soluble in organics and more easily hydrated, allowing higher incorporation of up to 30 mole percent of the anchor in the membrane whereas the phospholipid anchor could only be incorporated up to 10 mole percent lipid. Regardless, when calcein-loaded vesicles were incubated with 30% fetal bovine serum (FBS) at 37° C., all trehalose-polymer containing vesicles exhibited slower contents release than control vesicles with unfunctionalized lipid and similar zeta potential (FIG. 7).

The anhydrobiotic membrane preservation properties of the trehalose polymers on supported lipid bilayers (SLBs) were tested. It has been previously demonstrated that SLBs survive dehydration when dried from 20 weight percent aqueous trehalose solutions. We find that SLBs formed with 10 mole percent trehalose-phospholipid polymer may be hydrated with minimal loss of surface coverage and retention of membrane fluidity as judged by fluorescence recovery after photobleaching experiments. Moreover, lyophilized calcein-loaded trehalose-polymer vesicles could be rehydrated without contents loss and maintenance of vesicle size distribution. The cryo-preservative effects of trehalose and other sugars on proteins and membrane structures has been known for some time, though high solution concentrations are required; here we find that preservative properties at mole ratios of about 10% to about 30%. This preservative property permits long-term anhydrous storage of reagents without compromising therapeutic effect. Thus, membrane-anchored polysaccharides may be a useful biotechnology tool for production of systemic drug carriers that are stable to attack from serum proteins, dehydration and freeze-drying.

Example 2

Figures 8A, 8B:
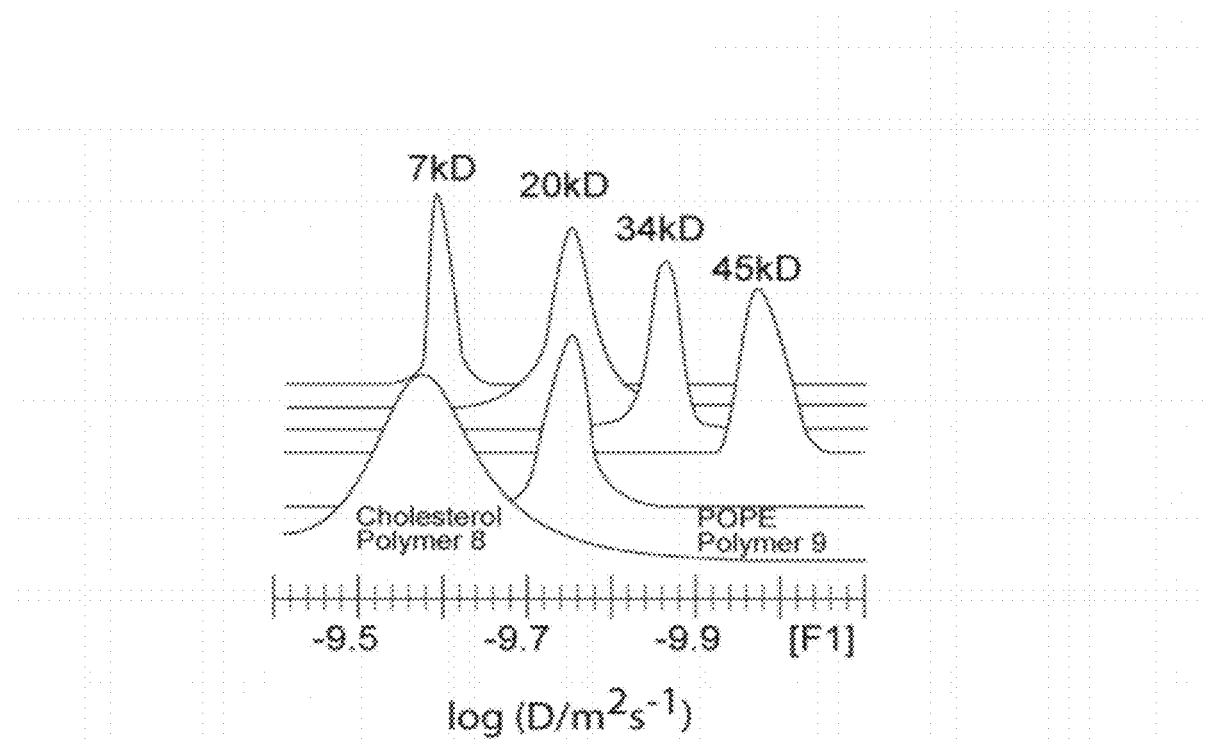
FIG. 8A is a graph illustrating diffusion coefficients of lipid vesicles in accordance with embodiments of the invention.
FIG. 8B is a table illustrating DLS and zeta potential of lipid vesicles in accordance with embodiments of the invention.

While in situ reaction of pre-formed vesicles containing aminooxyether lipids resulted in large vesicle aggregates, hydration of mixed lipid films containing defined mole fractions of oxime-linked glycolipids yielded well-behaved suspensions. Both oxime dimers and polymers were found to be stable at 37° C. at neutral pH (PBS) for several days, as monitored by mass spectroscopy. Polymer size, tunable by reaction time and concentration, was determined by diffusion ordered NMR (DOSY) using PMMA molecular weight standards for calibration (FIG. 8A). Larger (20 kD) cholesterol polymers were less soluble than the 7 kD cholesterol oligomer (Bhexamer) (8), while POPE-derived 20 kD polymer (~15mer) (9) and both sterol and POPE dimers (6 and 7, respectively) were soluble in methanol/chloroform mixtures. Organic solvent solubility permitted the preparation of mixed lipid films, which could be hydrated into vesicles. Notably, hydration and extrusion of a mixed lipid film containing ePC and either glycolipid polymer required elevated temperatures (50° C.) while ePC films are easily handled at room temperature. Neither polymer could be suspended in water in the absence of a lipid host environment. While this is unsurprising for the sterol polymer, we expected the phospholipid glycopolymer 9 to be more soluble. These altered properties may derive from the rigidity of the trehalose linker which may inhibit proper hydrophobic burial and suspension in water. Notably, the phospholipid dimer 7 could easily be hydrated to form a suspension, underscoring the differences in dimer and polymer of both physical properties and function.

Figure 8C:
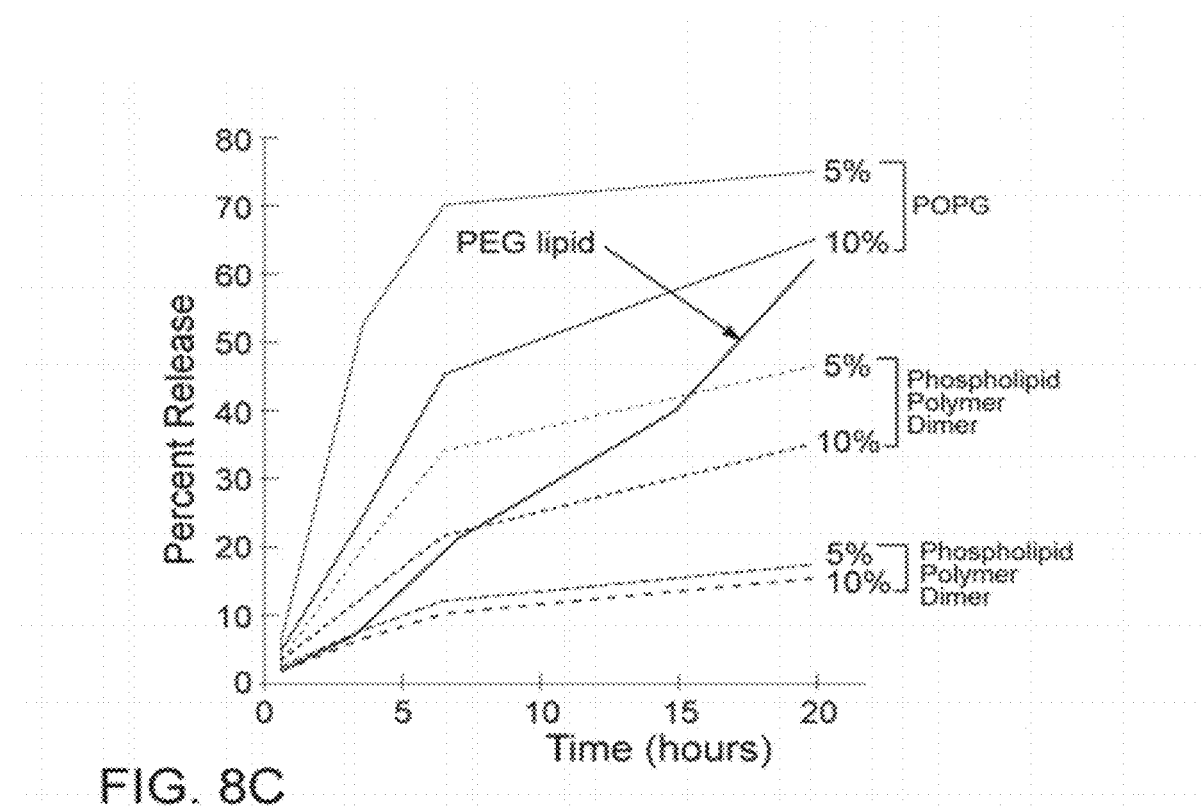
FIG. 8C is a graph illustrating the release of cargo over time from lipid vesicles in accordance with embodiments of the invention.
Figure 8D:
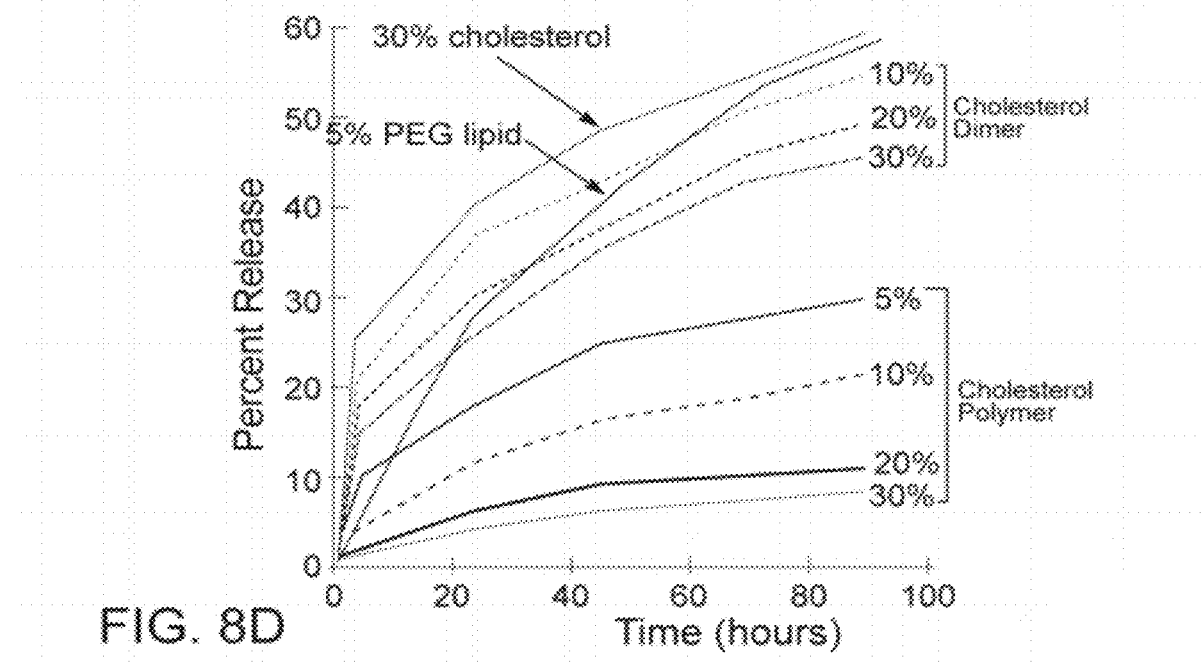
FIG. 8D is a graph illustrating the release of cargo over time from lipid vesicles in accordance with embodiments of the invention.

It has been shown that membranes with multiply-anchored cholesterol lipids exhibit enhanced stability. Consistent with these findings, cholesterol glycopolymer 8 in large, unilamellar vesicles (LUVs) provided the most effective stabilization in 30% fetal bovine serum at 37° C. as judged by a contents release assay (FIG. 8A-8D). The cholesterol and phospholipid anchored polymers 8 and 9, respectively, both yielded significant protection in FBS relative to controls, as did the respective trehalose-lipid dimers 6 and 7. The superior stabilization exhibited by the cholesterol-based glycopolymer likely derives from the greater inherent stability of cholesterol-containing membranes. The phospholipid series was compared to control LUVs wherein negatively charged phospholipid (POPG) replaced 20 kD the phospholipid glycopolymer 9, which has one negative charge per lipid anchor; indeed, phospholipid glycodimer 7 and phospholipid glycopolymer 9-LUVs had zeta potentials similar to LUVs containing the same mole fraction of POPG (FIG. 8B). Likewise, cholesterol dimer 6 and polymer 8-LUVs had sizes and low magnitude zeta potentials similar to LUVs composed of only zwitterionic PC and neutral cholesterol lipids. A fluid phase membrane composed of 70% egg PC (ePC) and 30 mole percent sterol (cholesterol/ 8) was used to allow release to be detected on the time scale of a few days (FIGS. 8C-8D). Vesicle stabilization by the glycolipid derivatives was strongly affected by degree of oligomerization and solubility. With both cholesterol and phospholipid anchors, the trehalose lipid dimers offered significant stabilization in FBS, but the polymeric trehalose-lipids always yielded superior protection per mole lipid anchor. Though there is clearly an advantage to structures larger than a dimer, larger oligomer or polymers may be limited by their ability to incorporate into the lipid membrane. Thus, it was difficult to achieve mole percent incorporation levels higher than 10% for phospholipid glycopolymer 9 and 30% for cholesterol glycopolymer 8.

Figure 9A:
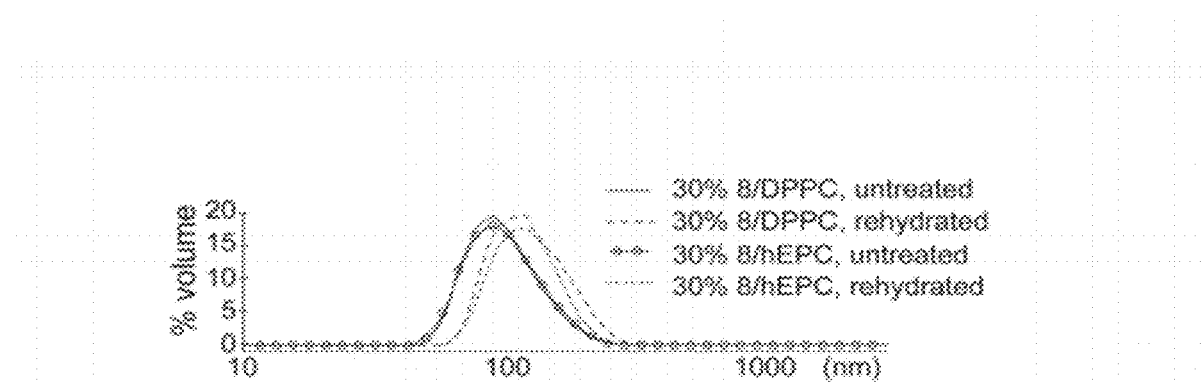
FIG. 9A is a graph illustrating resistance of lipid vesicles to being lyophilized and rehydrated in accordance with embodiments of the invention.
Figure 9B:
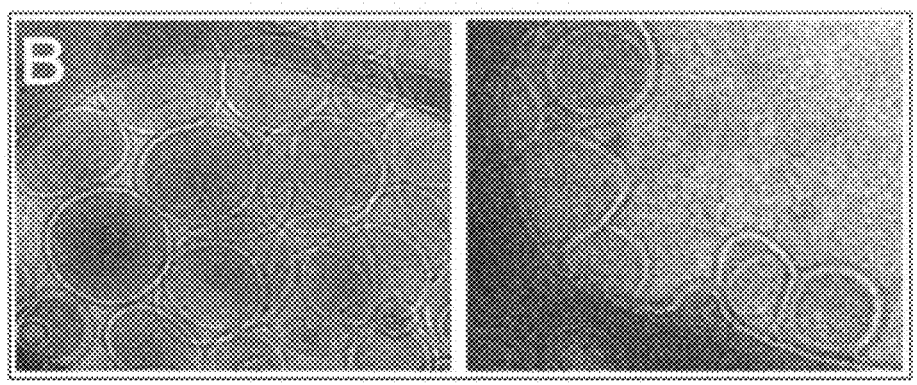
FIG. 9B include photomicrographs of lipid vesicles fresh hydrated (left panel) and after being lyophilized and rehydrated in accordance with embodiments of the invention.
Figure 9C:
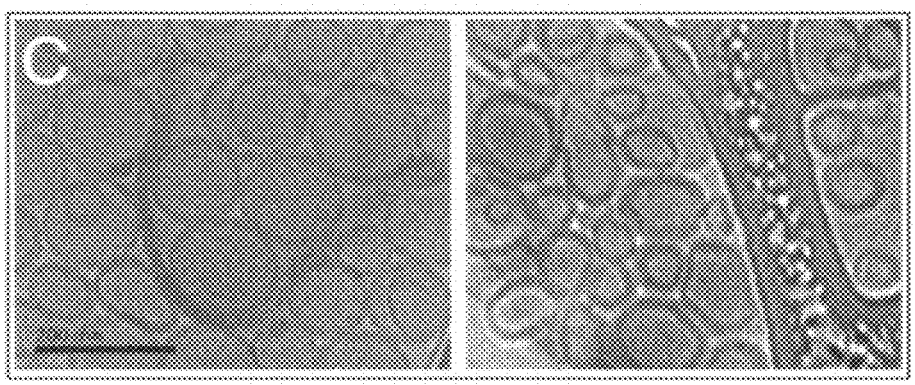
FIG. 9C include photomicrographs of lipid vesicles fresh hydrated (left panel) and after being lyophilized and rehydrated in accordance with embodiments of the invention.

A unique property of 30% cholesterol glycopolymer 8 in DPPC or hydrogenated ePC LUVs is that they may be lyophilized and rehydrated with minimal contents release (average of three trials was ~10% contents loss) when calcein dye was encapsulated; further, no significant changes in vesicular size or structure were observed by DLS (FIG. 9A) and cryo-TEM (FIGS. 9B and 9C). However, total contents loss and extensive fusion was observed when cholesterol or cholesterol glycodimer 6 was used in place of cholesterol glycopolymer 8, or if hydration was attempted at elevated temperatures (~70° C.). Sugar solutions (10:1 sugar:lipid) are known to protect LUVs from contents loss and fusion upon lyophilization and rehydration. It was find that covalent presentation of polymeric trehalose on multiple lipid anchors confers significant membrane anhydrobiotic and cryo-protection at sugar:lipid ratios of 0.1-0.3. Rehydration of freeze-dried gel phase LUVs without size change requires steric inhibition of vesicle fusion, which appears to be provided by the membrane-anchored trehalose-cholesterol oligomers. Cholesterol-polymer containing vesicles deposited poorly on glass, resulting in low yields of SLB formation. LUVs containing phospholipid glycodimer 7 and phospholipid glycopolymer 9 readily deposited, possibly by virtue of higher membrane fluidity.

Figure 10A:
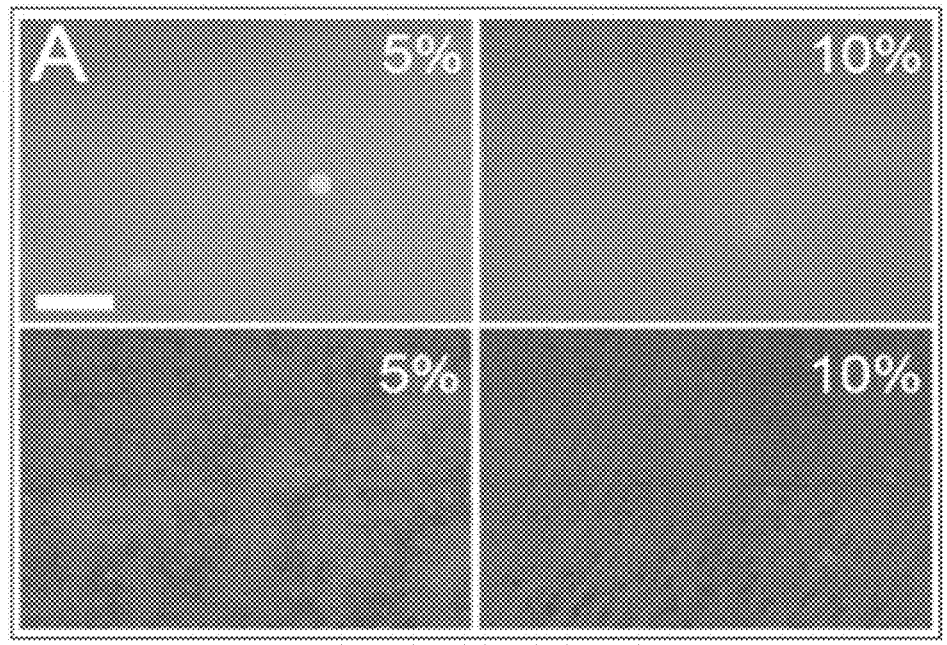
FIG. 10A shows photomicrographs of supported lipid bilayers containing phospholipid dimer in accordance with embodiments of the invention.
Figure 10B:
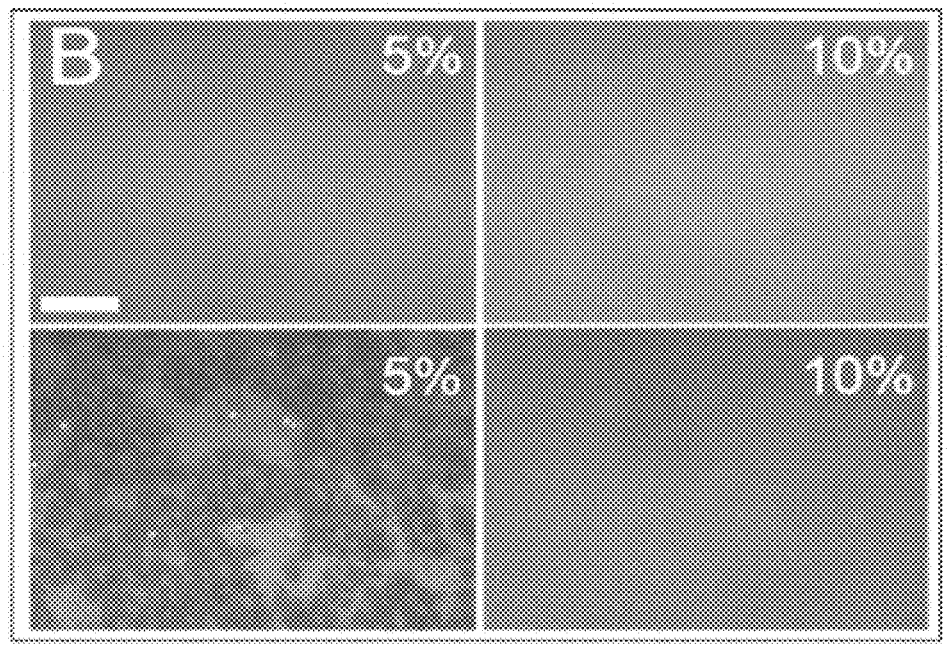
FIG. 10B shows photomicrographs of supported lipid bilayers containing phospholipid polymer in accordance with embodiments of the invention.
Figure 10C:
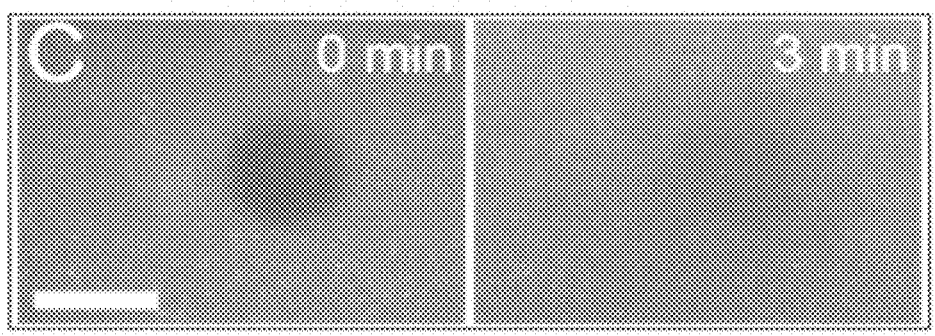
FIG. 10C shows photomicrographs of supported lipid bilayers containing phospholipid polymer in accordance with embodiments of the invention.
Figure 10D:
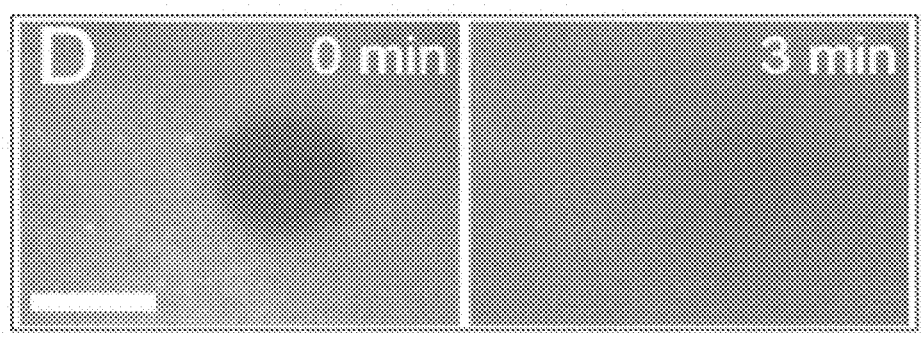
FIG. 10D shows photomicrographs of supported lipid bilayers containing phospholipid polymer in accordance with embodiments of the invention.

FIGS. 10A and 10B are photomicrographs of supported lipid bilayers containing (A) phospholipid dimer 7 or (B) phospholipid polymer. The mole percent is as indicated. The top rows of (A) and (B) show freshly formed SLBs; whereas the bottom rows show SLBs after drying and rehydration. The photos were taken at 10× magnification and the scale bar is 100 µm. FIGS. 10C and 10D show FRAP containing SLBs with 10% phospholipid polymer before and after dehydration, respectively. These photos were taken at 40× magnification and the scale bar is 40 µm. Though phospholipid glycodimer 7 preserved SLBs from delamination (uncoating from the glass surface) during dehydration-rehydration, considerable surface scarring occurred, whereas phospholipid glycopolymer 9 preserved both surface uniformity and membrane fluidity, as judged by fluorescence recovery after photobleaching (FRAP) at just 10 mole percent loading of 9 (FIG. 10A-10D), similar to prior reports of protection of lipid monolayers by synthetic trehalose lipids. As with vesicular membranes, phospholipid glycopolymer 9 offered superior anhydrobiotic SLB protection relative to phospholipid glycodimer 7, again suggesting that presentation of covalently clustered sugars as afforded by the polymeric structure of phospholipid glycopolymer 9 is beneficial.

Stabilization of membranes to physical insults over a wide range of hydration is important for the development of bilayer-based devices. The current method provides a strategy suitable for stabilization of free-standing membranes. As is clear, trehalose exhibits exceptional function among disaccharides with regard to protection against anhydrobiotic and cryogenic of SLBs, protein and vesicles, leading to its use in pharmaceutical formulations.

The glycolipid embodiments presented here allow access to neutral or charged glycolipid polymer membranes that have unique anhydrobiotic and cryogenic stability. PEG-protected vesicles are the only marketed immunoevasive liposomal drug carriers but cannot be freeze-dried without external protectant. Here, however, glycolipid polymers stabilize vesicular and supported lipid membranes to anhydrobiotic and cryogenic conditions, which has not been previously demonstrated with lipid polymerization or any other strategy. Thus, membrane protection with glycolipids and related biomaterials allow for unique delivery systems and membrane based devices.

Trehalose also possesses a number of unique physical properties: it has the largest hydrated radius of any disaccharide, the highest glass transition temperature, reversible, hydration-dependent polymorphism, and kosmotropic function in water. These physical properties are thought to allow trehalose to protect biomolecular assemblies (such as membranes) in a glassy solid sugar coating that is stable to varying hydration levels.

Example 3

Animal Study

Lipid vesicles were prepared using 80% DPPC and 20% trehalose cholesterol thioglycolate thioether dimer. The thioglycolate compound was found to protect supported lipid bilayers from delamination upon drying. Further, contents loss upon exposure to serum was greatly minimized. The vesicle preparation was loaded with doxorubicin using the remote loading method. These vesicles were used in the following animal study.

Wild type female C57Bl/6 mice were shaved on their left side and injected with 1×106 B16F10 murine malignant melanoma tumor cells. After 4 days, the tumors become palpable. Prior to the first treatment (Day 0), the mice are weighed and tumor measurements recorded using calipers. The initial tumor volumes are calculated using the formula for the volume of a spheroid: $V=4/3 \times pi \times ((\text{shortest diameter}2) \times (\text{longest diameter}))$. The mice were randomized into three treatment groups: 1) Vehicle (10 mM HEPES, 150 mM NaCl, Ph 7.4); 2) 2.5 mg/kg body weight Doxorubicin (High dose), and 3) 0.25 mg/kg body weight Doxorubicin (Low dose). Afterwards, the mice were anesthetized with isoflurane and intravenously-administered treatment using an insulin syringe. Mouse weights were measured every three days. Tumor measurements were collected daily. Treatment was repeated in the same manner at Day 7. The length of the trial was 14 days. Neither treatment nor the tumors had a significant effect on total mouse weight (Veh: 101%, DoxoHi: 93%, DoxoLow: 105%, respectively, of their weights on Day 0 or a significant difference between mouse groups).

Figure 11:
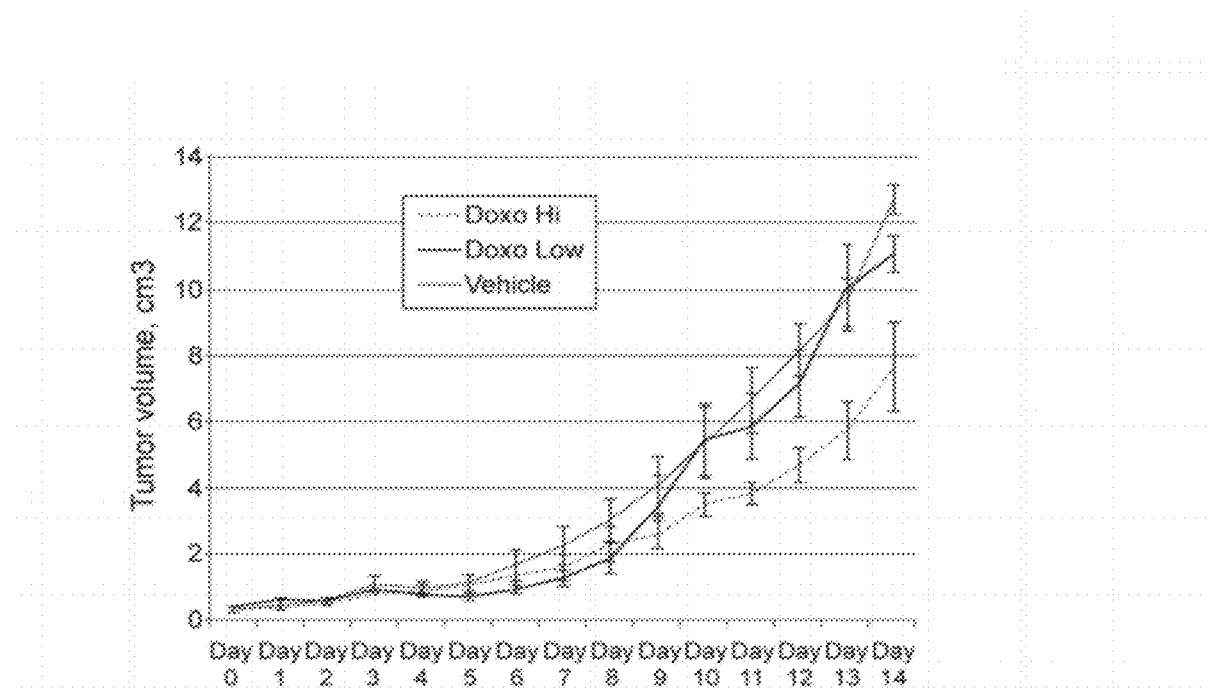
FIG. 11 is a graph illustrating the change in tumor volume of mice treated lipid vesicles in accordance with embodiments of the invention.

FIG. 11 shows a graph of tumor growth over the treatment period for the Doxirubicin containing nanoparticles and their inhibition of melanoma tumor growth invivo. N=5 mice per group. Error bars represent SEM.

Figure 12:
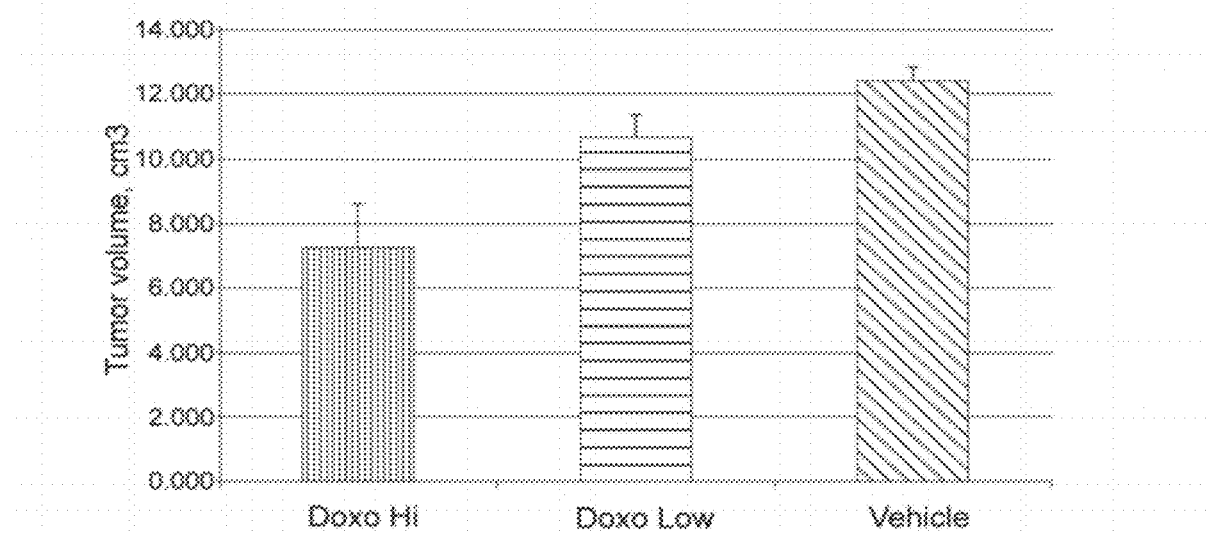
FIG. 12 is a graph illustrating the change in tumor volume of mice treated lipid vesicles in accordance with embodiments of the invention.

FIG. 12 shows a graph representing tumor size on the final day of testing. It is clear that the Doxorubucin-containing nanoparticles inhibit melanoma tumor growth in vivo. On day of sacrifice, the group of mice receiving the nanoparticles containing 2.5 mg/kg Doxorubucin (DoxoHI) and 0.25 mg/kg Doxorubucin (DoxoLow) had significantly smaller tumors than those mice receiving vehicle, p=0.0029 and p=0.018, respectively. Further, there was a statistical difference in final tumor volume between the DoxoHI group and the DoxoLow group, p=0.044. N=5 mice per group. Error bars represent SEM.

Figure 13:
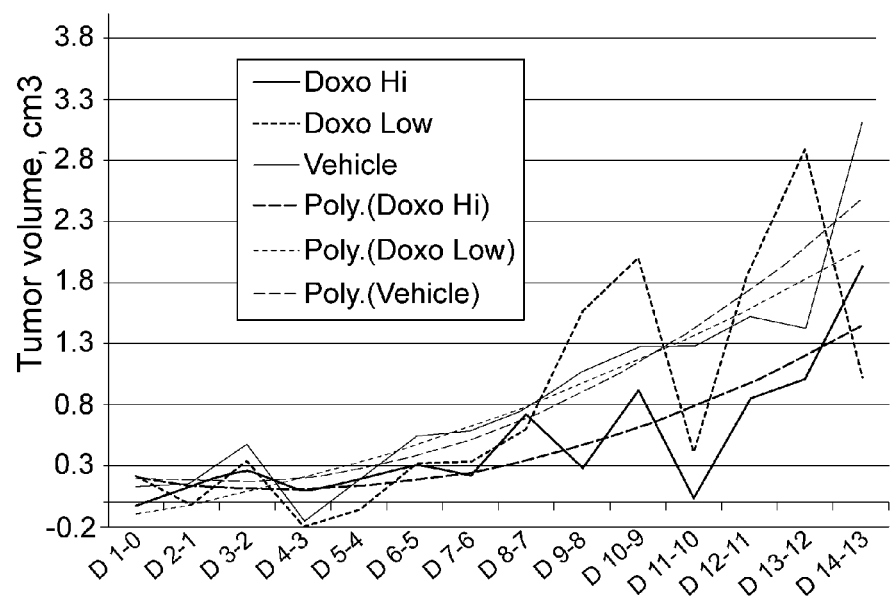
FIG. 13 is a graph illustrating the change in tumor volume of mice treated lipid vesicles in accordance with embodiments of the invention.

FIG. 13 shows a graph of data for tumor growth rates measured day-to-day. The tumor growth rates from one to day the next day. D1-0 represents the growth rate for the first day after treatment (Day 1 tumor volumes-Day 0 tumor volumes). Treatment was administered on Day 0 and Day 7.

While the present invention has been illustrated by the description of one or more embodiments thereof, and while the embodiments have been described in considerable detail, they are not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method and illustrative examples shown and described. Accordingly, departures may be made from such details without departing from the general inventive concept.

What is claimed is:

1. A surface stabilized synthetic membrane comprising:
   at least one lipid bilayer; and
   at least one sugar-anchor polymer coupled to the lipid bilayer by the anchor wherein the sugar-anchor polymer includes a first sugar having a first covalent bond to a first anchor and a second covalent bond to a second anchor, and a second sugar having a third covalent bond with at least one of the first anchor or the second anchor, wherein the first anchor and the second anchor are selected from the group consisting of a lipid and a peptide, and
   wherein the first, second, and third covalent bonds are selected from the group consisting of an oxime bond, a hydrazone bond, an acylhydrazide bond, an aminothioacetal bond, an acetal bond, a thioacetal bond, a dithioacetal bond, a thioether bond and combinations thereof.

2. The surface stabilized synthetic membrane of claim 1 wherein at least one of the first and second sugars are trehalose.

3. The surface stabilized synthetic membrane of claim 1 wherein at least one of the first anchor or the second anchor is selected from the group consisting of cholesterol and 1-palmitoyl-2-oleoyl-sn-glycero-3-phospho-ethanolamine (POPE).

4. The surface stabilized synthetic membrane of claim 1 wherein at least one of the first anchor or the second anchor is selected from the group consisting of a sterol anchor, a sphingosine derivative, a saturated phospholipid, a saturated diester lipid, a diether lipid, and combinations thereof.

5. The surface stabilized synthetic membrane of claim 1 further comprising a third sugar covalently having a covalent bond to the at least one of the first or second anchor that has the third covalent bond with the second sugar.

6. The surface stabilized synthetic membrane of claim 5 wherein the third sugar is trehalose.

7. The surface stabilized synthetic membrane of claim 1 wherein the first anchor has a first nucleophilic moiety, the second anchor has a second nucleophilic moiety, and the first sugar has a first electrophilic moiety and a second electrophilic moiety,
   wherein the first covalent bond is formed from the reaction of the first nucleophilic moiety with the first electrophilic moiety and the second covalent bond is formed from the reaction of the second nucleophilic moiety with the second electrophilic moiety.

8. The surface stabilized synthetic membrane of claim 7 wherein the nucleophilic moiety of at least one of the first anchor or the second anchor is selected from the group consisting of the following structural formulas:

Nu=X—Y  X=O, NH

Y=NH$_2$, NHCOR or

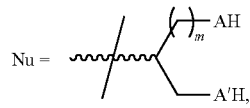

A, A' = O, N, S
m = 0 or 1 and
   the first sugar has the structural formula E-Su-E wherein Su represents a sugar and E represents an electrophilic moiety, and E has the structural formula:

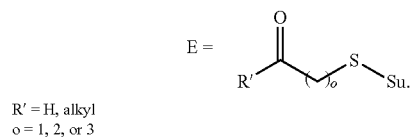
R′ = H, alkyl
o = 1, 2, or 3
9. The surface stabilized synthetic membrane of claim 7 wherein at least one of the first anchor or the second anchor is a lipid that further comprises one or two additional nucleophilic moieties.
* * * * *

UNITED STATES PATENT AND TRADEMARK OFFICE
CERTIFICATE OF CORRECTION

| | |
|---|---|
| PATENT NO. | : 9,446,147 B2 |
| APPLICATION NO. | : 13/404852 |
| DATED | : September 20, 2016 |
| INVENTOR(S) | : Dennis Bong |

It is certified that error appears in the above-identified patent and that said Letters Patent is hereby corrected as shown below:

In the Specification

Column 3, Line 41, reads "mers in accordance with embodiments of the inventors." and should read -- mers in accordance with embodiments of the invention. --

Column 3, Line 44, reads "mers in accordance with embodiments of the inventors." and should read -- mers in accordance with embodiments of the invention. --

Column 3, Line 47, reads "embodiments of the inventors." and should read -- embodiments of the invention. --

Column 3, Line 50, reads "inventors." and should read -- invention. --

Column 3, Line 52, reads "dimer in accordance with embodiments of the inventors." and should read -- dimer in accordance with embodiments of the invention. --

Column 3, Line 54, reads "in accordance with embodiments of the inventors." and should read -- in accordance with embodiments of the invention. --

Column 4, Line 1, reads "FIG. 9B include photomicrographs of lipid vesicles fresh" and should read -- FIG. 9B includes photomicrographs of lipid vesicles fresh --

Column 4, Line 4, reads "FIG. 9C include photomicrographs of lipid vesicles fresh" and should read -- FIG. 9C includes photomicrographs of lipid vesicles fresh --

Column 4, Line 40, reads "capable of coupling to complimentary linker moieties on at" and should read -- capable of coupling to complementary linker moieties on at --

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,446,147 B2

Column 6, Line 22, reads "moieties Nu of Lipids L is reacted with the electrophilic" and should read -- moieties Nu of Lipids L are reacted with the electrophilic --

Column 7, Line 24, reads "which allows coupling to the a nucleophilic moiety on the" and should read -- which allows coupling to a nucleophilic moiety on the --

Column 7, Line 38, reads "porated into a lipid membrane with either a pre-formed" and should read -- porated into a lipid membrane with either pre-formed --

Column 9, Line 10, reads "Another the cholesterol lipid anchor was used to form a" and should read -- Another cholesterol lipid anchor was used to form a --

Column 9, Line 43, reads "concentrations are required; here we find that preservative" and should read -- concentrations are required; here we find preservative --

Column 10, Line 56, reads "contents loss and extensive fusion was observed when" and should read -- contents loss and extensive fusion were observed when --

Column 10, Line 61, reads "fusion upon lyophilization and rehydration. It was find that" and should read -- fusion upon lyophilization and rehydration. It was found that --

Column 12, Line 29, reads "period for the Doxirubicin containing nanoparticles and their" and should read -- period for the Doxorubicin containing nanoparticles and their --

Column 12, Line 33, reads "day of testing. It is clear that the Doxorubucin-containing" and should read -- day of testing. It is clear that the Doxorubicin-containing --

Column 12, Lines 36-37, read "ticles containing 2.5 mg/kg Doxorubucin (DoxoHI) and 0.25 mg/kg Doxorubucin (DoxoLow) had significantly smaller" and should read -- ticles containing 2.5 mg/kg Doxorubicin (DoxoHI) and 0.25 mg/kg Doxorubicin (DoxoLow) had significantly smaller --

Column 12, Lines 44-45, read "measured day-to-day. The tumor growth rates from one to day the next day. D1-0 represents the growth rate for the" and should read -- measured day-to-day; the tumor growth rates from one day to the next day. D1-0 represents the growth rate for the --

In the Claims

At Claim 2, Column 13, Lines 54-56, read "2. The surface stabilized synthetic membrane of claim 1 wherein at least one of the first and second sugars are trehalose." and should read -- 2. The surface stabilized synthetic membrane of claim 1 wherein at least one of the first and second sugars is trehalose. --